United States Patent
Muraca

(10) Patent No.: US 9,732,158 B2
(45) Date of Patent: Aug. 15, 2017

(54) ANTIBODIES AGAINST FATTY ACID SYNTHASE

(71) Applicant: Nuclea Biotechnologies, Inc., Pittsfield, MA (US)

(72) Inventor: Patrick J. Muraca, Pittsfield, MA (US)

(73) Assignee: NMDX, LLC, Pittsfield, MA (US)

( * ) Notice: Subject to any disclaimer, the term of this patent is extended or adjusted under 35 U.S.C. 154(b) by 0 days.

(21) Appl. No.: 14/189,288

(22) Filed: Feb. 25, 2014

(65) Prior Publication Data

US 2014/0206018 A1    Jul. 24, 2014

Related U.S. Application Data

(62) Division of application No. 13/258,666, filed as application No. PCT/US2010/030545 on Apr. 9, 2010, now Pat. No. 8,729,239.

(60) Provisional application No. 61/167,985, filed on Apr. 9, 2009.

(51) Int. Cl.
| | | |
|---|---|---|
| *C07K 16/40* | (2006.01) | |
| *C07K 16/00* | (2006.01) | |
| *G01N 33/53* | (2006.01) | |
| *C12N 9/00* | (2006.01) | |
| *G01N 33/573* | (2006.01) | |
| *A61K 39/00* | (2006.01) | |

(52) U.S. Cl.
CPC ............... *C07K 16/40* (2013.01); *C12N 9/93* (2013.01); *G01N 33/573* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,665,874 A | 9/1997 | Kuhajda et al. | |
| 5,759,791 A | 6/1998 | Kuhajda et al. | |
| 5,759,837 A | 6/1998 | Kuhajda et al. | |
| 5,864,011 A | 1/1999 | Kuhajda et al. | |
| 5,872,217 A | 2/1999 | Kuhajda et al. | |
| 5,981,575 A | 11/1999 | Kuhajda et al. | |
| 7,622,260 B2 | 11/2009 | Gordon et al. | |
| 7,649,012 B2 | 1/2010 | Kuhajda et al. | |
| 7,732,491 B2 | 6/2010 | Sherman et al. | |
| 7,745,391 B2 * | 6/2010 | Mintz ................ | G06F 19/24 514/19.3 |
| 7,811,774 B2 | 10/2010 | Ring et al. | |
| 7,906,294 B2 | 3/2011 | Kinlaw, III | |
| 2003/0065156 A1 | 4/2003 | Williams et al. | |
| 2003/0138833 A1 | 7/2003 | Polyak et al. | |
| 2003/0175736 A1 | 9/2003 | Chinnaiyan et al. | |
| 2003/0219760 A1 | 11/2003 | Gordon et al. | |
| 2004/0018546 A1 | 1/2004 | Hung | |
| 2004/0029114 A1 | 2/2004 | Mack et al. | |
| 2005/0196754 A1 | 9/2005 | Drmanac et al. | |
| 2006/0034850 A1 | 2/2006 | Weidanz et al. | |
| 2007/0148718 A1 | 6/2007 | Medghalchi et al. | |
| 2007/0207975 A1 | 9/2007 | Menendez et al. | |
| 2008/0050278 A1 | 2/2008 | Farina et al. | |
| 2008/0056553 A1 | 3/2008 | Rimm et al. | |
| 2008/0103208 A1 | 5/2008 | Ossovskaya et al. | |
| 2009/0104617 A1 | 4/2009 | Gordon et al. | |
| 2009/0232818 A1 | 9/2009 | Kinlaw, III | |
| 2009/0304679 A1 | 12/2009 | Weidanz | |
| 2010/0158894 A1 | 6/2010 | Umemura et al. | |
| 2011/0059854 A1 | 3/2011 | Gordon et al. | |
| 2011/0124021 A1 | 5/2011 | Medghalchi | |
| 2011/0150876 A1 | 6/2011 | Kinlaw, III | |
| 2011/0195411 A1 | 8/2011 | Cao | |
| 2011/0237625 A1 | 9/2011 | Gaul et al. | |
| 2012/0065107 A1 | 3/2012 | Ring et al. | |
| 2012/0301467 A1 | 11/2012 | Medghalchi et al. | |

FOREIGN PATENT DOCUMENTS

| | | |
|---|---|---|
| WO | 9402108 A1 | 2/1994 |
| WO | 9519706 A1 | 7/1995 |
| WO | 97018806 A1 | 5/1997 |
| WO | 0160174 A2 | 8/2001 |
| WO | 0220736 | 3/2002 |
| WO | 02059373 A2 | 8/2002 |
| WO | 02089847 A1 | 11/2002 |
| WO | 03023355 A2 | 3/2003 |
| WO | 2004005277 A1 | 1/2004 |
| WO | 2004006835 A2 | 1/2004 |
| WO | 2004041189 A2 | 5/2004 |

(Continued)

OTHER PUBLICATIONS

Albertsen, et al., 20-year Outcomes Following Conservative Management of Clinically Localized Prostate Cancer, JAMA, May 4, 2005, vol. 293, No. 17, pp. 2095-2101.

Alo, et al. Immunohistochemical expression of human enrythrocyte glucose transporter and fatty acid synthase in infiltrating breast carcinomas and adjacent typical/atypical hyperplastic or normal breast tissue. Am J Clin Pathol. 2001, 116(1): 129-134.

Andersson, et al., Body Size and Prostate Cancer: a 20-year Follow-up Study Among 135006 Swedish Construction Workers, Mar. 5, 1997, vol. 89, No. 5, pp. 385-389.

Baron, et al., Fatty Acid Synthase: A Metabolic Oncogene in Prostate Cancer?, J Cell Biochem., Jan. 1, 2004, vol. 91, No. 1, pp. 47-53.

Bloom, et al. "Histological Grading and Prognosis in Breast Cancer; a Study of 1409 Cases of Which 359 Have Been Followed for 15 Years." Br J Cancer. 1957, 11(3): 359-377.

(Continued)

*Primary Examiner* — Sharon Wen

(57) ABSTRACT

The present invention relates to antibodies that immunospecifically bind to FAS and certain FAS related proteins. The invention encompasses human and humanized forms of the antibodies and their use in treating cancers and other proliferative disorders. The invention also relates to FAS-derived peptides useful for preparing the antibodies. Methods and compositions for detecting, diagnosing, treating or ameliorating a disease or disorder, especially cancer and other proliferative disorders using the present antibodies also are disclosed.

10 Claims, 4 Drawing Sheets

(56) References Cited

FOREIGN PATENT DOCUMENTS

| WO | 2004085621 A2 | 10/2004 |
|---|---|---|
| WO | 2005117590 A2 | 12/2005 |
| WO | 2007014247 A2 | 2/2007 |
| WO | 2007014249 A2 | 2/2007 |
| WO | 2007022475 A1 | 2/2007 |
| WO | 2008057585 A1 | 5/2008 |
| WO | 2008106563 A2 | 9/2008 |
| WO | 2009064927 A2 | 5/2009 |
| WO | 2009149066 A1 | 12/2009 |
| WO | 2010135475 A2 | 11/2010 |
| WO | 2011031517 | 3/2011 |

OTHER PUBLICATIONS

Calle, et al., Overweight, Obesity, and Mortality from Cancer in a Prospectively Studied Cohort of U.S. Adults, N Engl J Med., Apr. 24, 2003, vol. 348, No. 17, pp. 1625-1638.

Camassei, et al. "Expression of the Lipogenic Enzyme Fatty Acid Synthase (FAS) in Retinoblastoma and Its Correlation with Tumor Aggressiveness." Invest Ophthalmol Vis Sci. 2003, 44(6) pp. 2399-2403.

Campa, et al. "Genetic Variation in Genes of the Fatty Acid Synthesis Pathway and Breast Cancer Risk." Breast Cancer Res Treat. 2009, 118(3): 565-574.

Cerhan, et al., Cancer Mortality Among Iowa Farmers: Recent Results, Time Trends, and Lifestyle Factors (United States), Cancer Causes Control, May 1998, vol. 9, No. 3, pp. 311-319.

Chirala, et al., Animal Fatty Acid Synthase: Functional Mapping and Cloning and Expression of the Domain I Constituent Activities, Pro Natl Acad Sci U S A, May 27, 1997, vol. 94, No. 11, pp. 5588-5593.

De Schrijver, et al., RNA Interference-mediated Silencing of the Fatty Acid Synthase Gene Attenuates Growth and Induces Morphological Changes and Apoptosis of LNCaP Prostate Cancer Cells, Cancer Res., Jul. 1, 2003, vol. 63, No. 13, pp. 3799-3804.

Epstein, et al., OA-519 (Fatty Acid Synthase) As an Independent Predictor of Pathologic Stage in Adenocarcinoma of the Prostate. Urology, Jan. 1995, vol. 45, No. 1, pp. 81-86.

Heemers, et al., Androgens stimulate lipogenic gene expression in prostate cancer cells by activation of the sterol regulatory element-binding protein cleavage activating protein/sterol regulatory element-binding protein pathway, Mol Endocrinol., 2001, vol. 15, No. 10, pp. 1817-1828.

International Search Report for International Application No. PCT/US2012/060187, dated Apr. 15, 2013.

Kridel, et al., Orlistat is a Novel Inhibitor of Fatty Acid Synthase with Antitumor Activity, Cancer Res., Mar. 15, 2004, vol. 64, No. 6, pp. 2070-2075.

Kuhajda, et al., Fatty acid synthesis: a potential selective target for antineoplastic therapy, Proc Natl Acad Sci U S A, Jul. 5, 1994, vol. 91, No. 14, pp. 6379-6383.

Kuhajda, et al., Synthesis and Antitumor Activity of an Inhibitor of Fatty Acid Synthase, Proc Natl Acad Sci U S A, Mar. 28, 2000, vol. 97, No. 7, pp. 3450-3454.

Kuhajda, Fatty-acid synthase and human cancer: new perspectives on its role in tumor biology, Nutrition, Mar. 2000, vol. 16, No. 3, pp. 202-208.

Ookhtens, et al., Liver and adipose tissue contributions to newly formed fatty acids in an ascites tumor, Am J Physiol., Jul. 1984, vol. 247, No. 1, Pt 2, pp. R146-R153.

PCT International Search Report dated Sep. 14, 2010 for International Application No. PCT/US2010/030545.

PCT Written Opinion dated Sep. 14, 2010 for International Application No. PCT/US2010/030545.

Rossi, et al., Fatty Acid Synthase Expression Defines Distinct Molecular Signatures in Prostate Cancer, Mol Cancer Res., Aug. 2003, vol. 1, No. 10, pp. 707-715.

Sabine, et al., Control of Lipid Metabolism in Hepatomas: Insensitivity of Rate of Fatty Acid and Cholesterol Synthesis by Mouse Hepatome BW7756 to Fasting to Feedback Control, Cancer Res., Apr. 1967, vol. 27, No. 4, pp. 793-799.

Shah, et al., Fatty acid synthase gene over expression and copy number gain in prostate adenocarcinoma, Hum Pathol., Apr. 2006, vol. 37, No. 4, pp. 401-409.

Shurabji, et al., Immunohistochemical Detection of a Fatty Acid Synthase (OA-519) as a Predictor of Progression of Prostate Cancer. Human Pathology, vol. 27, No. 9. Sep. 1996, pp. 917-921.

Smotrys, et al., Palmitoylation of intracellular signaling proteins: regulation and function, Annual Rev Biochem., 2004, vol. 73, pp. 559-587.

Snowdon, Diet, Obesity, and Risk of Fatal Prostate Cancer, Am J Epidemiol., Aug. 1984, vol. 120, No. 2, pp. 244-250.

Sorlie, et al. "Distinct Molecular Mechanisms Underlying Clinically Relevant Subtypes of Breast Cancer: Gene Expression Analyses Across Three Different Platforms." BMC Genomics 2006, 7: 127, pp. 1-15.

Swinnen, et al., Androgens Stimulate Fatty Acid Synthase in the Human Prostate Cancer Cell Line LNCaP, Cancer Res., 1997, vol. 57, No. 6, pp. 1086-1090.

Swinnen, et al., Fatty acid synthase drives the synthesis of phospholipids partitioning into detergent-resistant membrane microdomains, Biochem Biophys Res Commun., Mar. 21, 2003, vol. 302, No. 4, pp. 898-903.

Swinnen, et al., Selective activation of the fatty acid synthesis pathway in human prostate cancer. Int J Cancer, Oct. 15, 2000, vol. 88, No. 2, pp. 176-179.

Wang, et al "Two-site ELISA for the quantitative determination of fatty acid." Clinica Chimica Acta 2001, 304: 107-115.

Wang, et al. "Fatty acid synthase (FAS) expression in human breast cancer cell culture supernatants and in breast cancer patients." Cancer Lett. 2001, 167(1): 99-104.

Weiss, et al., Fatty-acid biosynthesis in man, a pathway of minor importance. Purification, optimal assay conditions, and organ distribution of fatty-acid synthase, Biol Chem Hoppe Seyler, Sep. 1986, vol. 367, No. 9, pp. 905-912.

Wright, et al., Prospective Study of Adiposity and Weight Change in Relation to Prostate Cancer Incidence and Mortality, Cancer, Feb. 15, 2007, vol. 109, No. 4, pp. 675-684.

Xiang et al., AMP-activated protein kinase activators can inhibit the growth of prostate cancer cells by multiple mechanisms. Biochemical and Biophysical Research Communications 321 (2004) pp. 161-167.

Yamauchi et al., Adiponectin stimulates glucose utilization and fatty-acid oxidation by activating AMP-activated protein kinase. Nature Medicine, vol. 8, No. 11, Nov. 2002.

Yang, et al. "Activity-based proteome profiling of potential cellular targets of Orlistat—an FDA-approved drug with anti-tumor activities." J Am Chem Soc. 2010, 132(2): 655-666; p. 656-666.

Yang, et al., Activation of fatty acid synthesis during neoplastic transformation: role of mitogen-activated protein kinase and phosphatidylinositol 3-kinase, Exp Cell Res., Sep. 10, 2002, vol. 279, No. 1, pp. 80-90.

* cited by examiner

SEQUENCE LISTING

```
<160> NUMBER OF SEQ ID NOS: 5

<210> SEQ ID NO 1
<211> LENGTH: 13
<212> TYPE: PRT
<213> ORGANISM: Human
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1

Val Ala Gln Gly Gln Trp Glu Pro Ser Gly Xaa Ala Pro
1               5                   10

<210> SEQ ID NO 2
<211> LENGTH: 13
<212> TYPE: PRT
<213> ORGANISM: Human
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Pro Ser Gly Pro Ala Pro Thr Asn Xaa Gly Ala Leu Glu
1               5                   10
```

```
<210> SEQ ID NO 3
<211> LENGTH: 13
<212> TYPE: PRT
<213> ORGANISM: Human
<220> FEATURE:
<221> NAME/KEY: misc_feature
<222> LOCATION: (7)..(7)
<223> OTHER INFORMATION: Xaa can be any naturally occurring amino acid

<400> SEQUENCE: 3

Thr Leu Glu Gln Gln His Xaa Val Ala Gln Gly Gln Trp
1               5                   10

<210> SEQ ID NO 4
<211> LENGTH: 16
<212> TYPE: PRT
<213> ORGANISM: Human

<400> SEQUENCE: 4

Glu Val Asp Pro Gly Ser Ala Glu Leu Gln Lys Val Leu Gln Gly Asp
1               5                   10                  15

<210> SEQ ID NO 5
<211> LENGTH: 14
<212> TYPE: PRT
<213> ORGANISM: Human

<400> SEQUENCE: 5

Glu Leu Ser Ser Lys Ala Asp Glu Ala Ser Glu Leu Ala Cys
1               5                   10
```

ANTIBODIES AGAINST FATTY ACID SYNTHASE

CROSS REFERENCE TO RELATED APPLICATIONS

This Patent Application is a Divisional application of U.S. patent application Ser. No. 13/258,666 filed on Sep. 22, 2011, which is US National Phase Application of PCT Patent Application No. PCT/US2010/030545 filed on Apr. 9, 2010, entitled "ANTIBODIES AGAINST FATTY ACID SYNTHASE," which is a PCT International Application claiming the benefit under 35 U.S.C. §119(e) of U.S. Patent Application No. 61/167,985 filed on Apr. 9, 2009, entitled, "ANTIBODIES AGAINST FATTY ACID SYNTHASE," the contents and teachings of which are hereby incorporated by reference in their entirety.

REFERENCE TO SEQUENCES

The instant application is being filed along with a Sequence Listing in electronic format. The Sequence Listing file, entitled 20151009USDIVSEQLST.txt, was created on Feb. 10, 2014 and is 1,589 bytes in size. The information in electronic format of the Sequence Listing is incorporated herein by reference in its entirety.

FIELD OF THE INVENTION

The present invention relates to antibodies and related molecules that immunospecifically bind to and inhibit the activity of fatty acid synthase and related pathway proteins. The invention relates to methods and compositions for preventing, detecting, screening, diagnosing, treating or ameliorating a proliferative disease using the present antibodies.

BACKGROUND OF THE INVENTION

Fatty acid synthase (FAS) is a 270 kDa cytosolic protein that functions as a homodimer (7). FAS catalyzes the synthesis of palmitate from the condensation of malonyl-CoA and acetyl-CoA, and also plays an important role in energy homeostasis by converting excess carbon intake into fatty acids for storage. When necessary, these fatty acids provide energy via β-oxidation (8). Most fatty acids are supplied by diet, so endogenous synthesis usually is minimal. Consequently, FAS is expressed at low to undetectable levels in most normal human tissues.

In contrast, FAS is over expressed in a large number of human cancers, including cancer of the prostate, despite high levels of ambient fatty acids (8). Almost all fatty acids in tumor cells are produced via de novo synthesis, despite adequate nutritional supply (14-17). The principal enzymatic product of FAS is palmitic acid. Palmitoylation, as well as other lipid modifications such as myristoylation, represent key regulatory switches in most signal transduction pathways including the phosphatidylinositol 3'-kinase (PI3K) and the Wnt/β-catenin pathways.

FAS and Prostate Cancer

The prevalence of prostate cancer is extremely high and increases with age; one in 6 men in the US will be diagnosed with prostate cancer during his lifetime. Prostate cancer is a leading cause of male cancer-related death, second only to lung and colon cancer, and represents about 10% of all cancer deaths in men in the United States (1). Multiple factors contribute to the high incidence and prevalence of prostate cancer. Risk factors include age, family history and race but also high fat diet and obesity (2-6). In fact, higher body mass index (BMI) and adult weight gain increase the risk of dying from prostate cancer (6). Dietary intervention or regulation of metabolic pathways can therefore potentially affect prostate cancer incidence and perhaps tumor aggressiveness.

It has been shown that the FAS enzyme is over expressed throughout the natural history of a substantial proportion of prostate cancers beginning with prostatic intraepithelial neoplasia, and that its increased expression is associated with a distinctive gene expression signature (9). Experimental studies have shown that FAS inhibitors or RNA interference-mediated silencing of FAS induce apoptosis in various tumor cell lines and/or tumor xenografts in vivo (10, 11).

It has been shown that one-fourth of human prostate cancers have genomic amplification of FAS (12). This suggests that FAS over expression confers a selective growth advantage to tumor cells. The biochemical and metabolic basis for and consequences of this over expression are not well understood. Prostate adenocarcinomas over expressing FAS display aggressive biologic behavior (13). Among the theories put forth for the role of FAS in carcinogenesis is the altered composition of membrane phospholipids (13), possibly altering detergent-resistant membrane microdomains (lipid rafts) and, as a result, signal transduction. Formal proof of this mechanism has not been obtained even though it has been shown that the majority (85%) of de novo synthesized fatty acids end up in cell membranes (18). The principal enzymatic product of FAS is palmitic acid. Indeed, many of the effects that result from FAS inhibition by cerulenin can be partially rescued by palmitic acid (10, 19). Therefore, it has been hypothesized that lipid-based post-translational modification of proteins for signal transduction pathways, such as ras or wnt palmitoylation, may confer a selective proliferative or survival advantage to cancer cells (20).

SUMMARY OF THE INVENTION

The invention comprises antibodies that specifically target FAS as well as certain FAS related proteins, peptides useful for generating the antibodies, and diagnostic, prognostic and therapeutic methods of using the antibodies. The antibodies of the present invention are specific for a peptide sequence conserved among FAS and some FAS-related proteins. The antibodies of the present invention preferentially recognize peptides and proteins containing at least a portion of the peptide sequence in a manner substantially independent of the surrounding amino acid sequence. In a preferred aspect, the invention comprises monoclonal antibodies that specifically inhibit overproduction, but not normal production, of FAS.

The present monoclonal antibodies may be raised in a mammalian species or may be produced in vitro. In one embodiment, the monoclonal antibodies of the present invention are raised by immunizing the mammal with a peptide or mixture of peptides derived from a FAS protein. In another embodiment, the monoclonal antibodies are prepared by an in vitro process using cells. In a preferred embodiment, the present monoclonal antibodies are humanized or human. The immunogenic peptides used to raise the antibodies also form a part of this invention.

Monoclonal anti-FAS antibodies of the present invention include monoclonal antibodies or antibody fragments, half-antibodies, hybrid derivatives, probes, and other molecular constructs. These antibodies binding portions thereof, probes, or ligands, are highly specific for FAS or FAS pathway proteins. Humanized or human monoclonal antibodies of the present invention are useful as therapeutic agents for treating neoplastic or proliferative diseases in which aberrant expression, particularly overexpression, of FAS is implicated.

The invention further comprises polyclonal antibodies raised using the immunogenic peptides of the invention. The monoclonal and polyclonal antibodies of the present invention may be used as diagnostic or prognostic reagents. In this embodiment, the antibodies may be included in a kit for use in an immunohistochemistry procedure.

Another aspect of the present invention relates to methods of detecting cancerous tissue in a biological sample. This method involves contacting a biological sample of a person suspected of having cancer with an anti-FAS antibody of the present invention labeled with a detectable label. The biological sample is contacted with the antibody having a label under conditions effective to permit binding of the antibody to the cancerous tissue in the biological sample. The presence of cancerous tissue in the biological sample is detected by detection of the label. For this purpose, the antibody may be monoclonal or polyclonal.

DETAILED DESCRIPTION OF THE INVENTION

Figure 1:
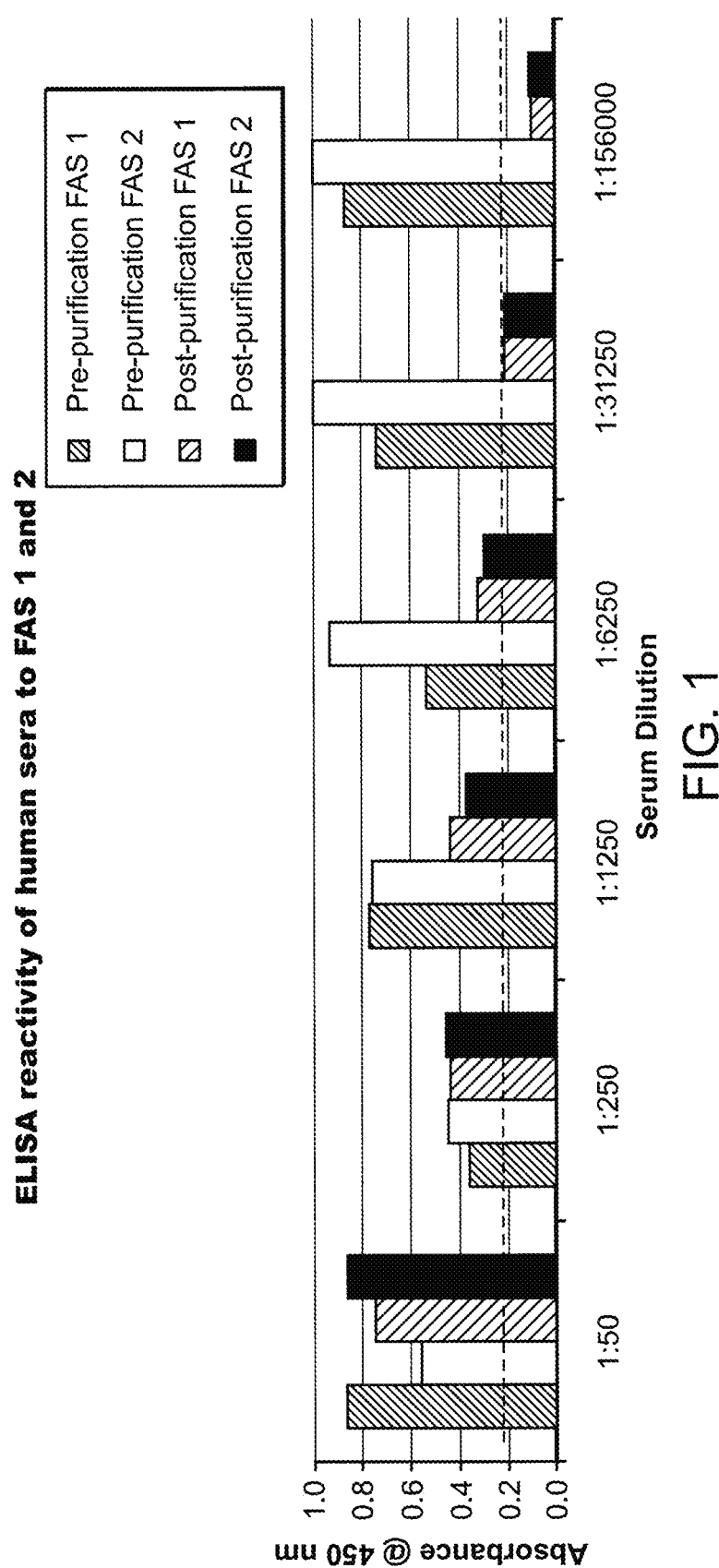
FIG. 1 is a graph showing the results of an ELISA assay using monoclonal antibodies of the present invention raised against the peptide of SEQ. ID NOs. 1 and 2 as the capture antibody. For each dilution, the two left columns represent the pre-purification MAbs, and the two right columns represent the post-purification MAbs.

The present invention encompasses antibodies, including antibody fragments, that immunospecifically bind to a FAS protein, fragment or a variant of FAS, as well as certain FAS related pathway proteins. In particular, the invention encompasses antibodies or fragments thereof that immunospecifically bind to a FAS protein comprising at least about six consecutive amino acids up to the full length of any of the polypeptides of SEQ ID NOs. 1-5.

In one aspect, the present invention relates to methods and compositions for preventing, treating or ameliorating a disease or disorder characterized by abnormal proliferation of cells comprising administering to an animal, preferably a human, a therapeutically effective amount of one or more monoclonal antibodies or fragments thereof that immunospecifically bind to and inhibit a FAS protein or polypeptide sequence, or variant thereof. In a preferred embodiment, the present invention relates to methods and compositions for preventing, treating or ameliorating a disease or disorder associated with FAS function or aberrant FAS expression, comprising administering to an animal, preferably a human, a therapeutically effective amount of one or more monoclonal antibodies or fragments thereof that immunospecifically bind FAS or a variant thereof. The preferred FAS antibodies are specific for all or a portion of the peptide sequence of SEQ ID NOs. 1-5.

In a preferred embodiment, human or humanized monoclonal antibodies of the present invention are used in methods and compositions for preventing, treating or ameliorating cancer, including but not limited to, the following types of cancer: breast cancer, lung cancer, colon cancer, cancer of the urinary tract, bladder cancer, kidney cancer, pancreatic cancer, liver cancer, stomach cancer, prostate cancer, leukemia, Non-Hodgkin's lymphoma, esophageal cancer, brain cancer, leukemia, ovarian cancer, testicular cancer, melanoma, uterine cancer, cervical cancer, cancer of the larynx, rectal cancer, and cancers of the oral cavity. In a preferred embodiment, the cancer is characterized by aberrant expression of FAS. In a highly preferred embodiment, the present invention relates to antibody-based methods and compositions for preventing, treating or ameliorating prostate cancer, especially forms of prostate cancer that are characterized by aberrant expression of FAS.

Preferably, the patient is tested for FAS expression prior to treatment. Testing may be carried out on a sample of the patient's tumor using standard immunohistochemistry techniques with the antibodies of the present invention, or a commercial antibody that detects FAS expression. The antibodies of the present invention may be administered alone, or in combination with chemotherapeutic agents such as paclitaxel (Taxol®), 5-fluororuracil (5-FU, Adrucil®), cyclophosphamide (Cytoxan®), cerulenin, methotrexate, or other therapeutic agents useful in the treatment of cancers.

The present invention also encompasses methods and compositions for detecting, diagnosing, or prognosing diseases or disorders comprising administering to an animal, preferably a human, an effective amount of an antibody or fragment thereof that immunospecifically binds to FAS or variant thereof, or to certain FAS pathway proteins, comprising at least a portion of the sequence of a peptide of SEQ ID NO. 1-5. The present invention also encompasses methods and compositions for detecting, diagnosing, or prognosing diseases or disorders associated with FAS function or aberrant FAS expression, comprising administering to an animal, preferably a human, an effective amount of an antibody or fragment thereof that immunospecifically binds to FAS or a variant thereof comprising at least a portion of the sequence of a peptide of SEQ ID NO. 1-5. In a preferred embodiment, the disease is cancer or other proliferative disorder characterized by aberrant expression of FAS. In a highly preferred embodiment, the disease is prostate cancer.

In preferred aspect, the antibodies are human or humanized monoclonal antibodies that are suitable for human therapeutic use. The present monoclonal antibodies are highly specific for FAS, which is implicated in many cancers. The monoclonal antibodies of the present invention further encompass fragments or variants of these antibodies (e.g., VH domains, VH CDRs, VL domains, or VL CDRs), that immunospecifically bind to, and inhibit, FAS or variants thereof comprising at least a portion of the sequence of a peptide of SEQ ID NO. 1-5. The present monoclonal antibodies or fragments thereof also may bind to and inhibit the activity of certain FAS-related proteins that contain at least a portion of the sequence of a peptide of SEQ ID NO. 1-5.

The present invention also comprises non-human monoclonal antibodies and polyclonal antisera that bind FAS which can be used as diagnostic or prognostic reagents. The non-human antibodies of the present invention may be linked to a detectable label, such as an enzyme, a fluorescent label, a luminescent label, or a bioluminescent label. The present invention also provides antibodies that bind FAS polypeptides which are coupled to a therapeutic or cytotoxic agent. The present invention also provides antibodies that bind FAS polypeptides which are coupled to a radioactive material.

Another aspect of the present invention comprises methods of using of the antibodies of the present invention as a diagnostic tool to monitor the expression of FAS in vitro, e.g., in a tumor biopsy specimen, using immunohistochemistry techniques.

The antibodies of the present invention can be produced by using well-established techniques for producing monoclonal and polyclonal antibodies, using the FAS peptides of SEQ ID NO. 1-5 as immunogens.

FAS Peptides

The present invention provides novel isolated FAS peptides, as well as mixtures containing two or more FAS peptides.

As used herein, the term "peptide" refers to a natural or synthetic molecule comprising two or more amino acids linked by the carboxyl group of one amino acid and the amino group of another. A peptide of the present invention is not limited by length, thus the term encompasses "polypeptide" and "protein." A "FAS peptide" of the present invention is a peptide fragment derived from a fatty acid synthase protein and is preferably between about 6 to about 100 amino acids in length, more preferably between about 8 to about 50 amino acids in length, more preferably between about 10 to about 35 amino acids in length. The terms "polypeptide" and "protein" sometimes are used interchangeably. A "FAS polypeptide" may refer to an entire FAS protein, or to a fragment or variant thereof. Preferably, the FAS peptides of the present invention contain an epitope for the production of an antibody specifically immunoreactive to the FAS peptide.

In a preferred embodiment, the peptides of the present invention comprise a peptide containing an epitope, either an immunogenic epitope or an antigenic epitope. An "immunogenic epitope" as used herein, refers to a portion of a peptide that elicits an antibody response in an animal, as determined by any method known in the art, for example, by the methods for generating antibodies described herein. See, for example, Geysen et al., 1983, *Proc. Natl. Acad. Sci. USA*, 81:3998-4002. The term "antigenic epitope" as used herein refers to a portion of a protein to which an antibody can immunospecifically bind to its antigen as determined by any method well known in the art, for example, by the immunoassays described herein. Antigenic epitopes need not necessarily be immunogenic. Peptides that function as epitopes may be produced by any conventional means. See, e.g., Houghten, 1985, *Proc. Natl. Acad. Sci. USA*, 82:5131-5135; and as described in U.S. Pat. No. 4,631,211.

As used herein, the term "isolated," with respect to peptides, nucleic acids, or antibodies, refers to that the material is removed from its original environment (e.g., the natural environment if it is naturally occurring). For example, a naturally-occurring nucleic acid or peptide or antibody present in a living animal is not isolated, but the same nucleic acid or peptide or antibody, which is separated from some or all of the coexisting materials in the natural system, is isolated. Such isolated nucleic acid could be part of a vector and such isolated nucleic acid or peptide or antibody could be part of a composition, and still be isolated in that the vector or composition is not part of its natural environment. An "isolated" peptide, nucleic acid or antibody, also includes material synthesized, or produced by recombinant DNA technology, as well as preparations such as serum containing an antibody of the invention.

In one embodiment, the FAS peptide of the invention is synthesized by methods known in the art and as described below. In another preferred embodiment, the FAS peptide is produced by expressing a nucleic acid encoding the peptide in a cell.

FAS peptides can be synthesized by methods well known in the art. Synthetic methods that can be used include, for example, ribosomally-directed fermentation methods, as well as non-ribosomal strategies and chemical synthesis methods. FAS peptides containing the 20 natural amino acids can be prepared via recombinant expression systems that utilize the ribosomally directed peptide synthesis machinery of a host organism, e.g., *E. coli*. Alternatively, FAS peptides, including those containing unnatural or non-proteninogenic amino acids or modified amino acid side chains can be prepared through a solution-phase chemical synthesis of peptides (e.g., using N-Boc protection and the activated ester route). Protocols for sequence solution-phase chemical synthesis of peptides have been described in Andersson et al., *Biopolymers*, 55:227-250 (2000). One method used for generating peptides is solution-phase chemical synthesis, which employs a N-tert-butoxy (N-Boc) protected amino acid and a C-protected amino acid. Andersson et al., supra. An alternative solution-phase method for chemically-catalyzed peptide synthesis employs pre-activated esters as the carboxyl component for coupling Andersson et al., supra. In addition, enzyme-mediated solid-phase peptide synthesis has also been employed. Solid-phase peptide synthesis (SPPS) uses insoluble resin supports, and has simplified and accelerated peptide synthesis and facilitated purification. Merrifield, R. B., *J. Am. Chem. Soc.*, 85:2149-2154 (1963). Since the growing peptide is anchored on an insoluble resin, unreacted soluble reagents can be removed by simple filtration or washing without manipulative losses. Solid phase peptide synthesis can be performed using automation. Those skilled in the art will recognize that various peptides are within the spirit and scope of the present invention.

The FAS peptides according to the present invention can be modified, for example, by the addition of an acetyl or amine group or amino acids at the amino- and/or carboxy-terminus of the peptide. Amino acid addition modifications may also be performed, for example, to alter the conformation of the epitope bearing peptide such that the epitope will have a conformation more closely related to the structure of the epitope in the native protein. An example of a modified epitope-bearing peptide of the invention is a peptide in which one or more cysteine residues have been added to the peptide to allow for the formation of a disulfide bond between two cysteines, thus resulting in a stable loop structure of the epitope-bearing peptide under non-reducing conditions. Disulfide bonds can form between a cysteine residue added to the peptide and a cysteine residue of the naturally-occurring epitope, or between two cysteines which have both been added to the naturally-occurring epitope-bearing peptide.

In addition, it is possible to modify one or more amino acid residues of the peptide by substitution with cysteines to promote the formation of disulfide bonded loop structures. Cyclic thioether molecules of synthetic peptides can be routinely generated using techniques known in the art, e.g., as described in PCT publication WO 97/46251, incorporated in its entirety by reference herein. Other modifications of epitope-bearing peptides contemplated by this invention include biotinylation.

In one embodiment, the FAS peptides of the invention is modified by adding an acetyl group at the amino terminus and/or an amide group at the carboxyl terminus.

The FAS peptides of the invention may be provided as a chimeric peptide, such as in the form of a fusion peptide. For instance, the FAS peptide can be provided as a recombinant fusion peptide which includes a second peptide portion having an amino acid sequence unrelated (heterologous) to the FAS peptide. For example, the second peptide portion may be glutathione-S-transferase, or a peptide with an enzymatic activity such as alkaline phosphatase, or an epitope tag.

In a preferred embodiment, the FAS peptide contains an amino acid sequence that is identical with or homologous to all or a portion containing at least about six consecutive amino acids of a sequence represented by any one of SEQ ID NOs. 1-5. A homologous sequence is at least about 70%, 75%, 80%, 85%, 90% or 95% identical to the peptide represented by any one of SEQ ID NOs. 1-5.

```
FAS Peptides:
                        SEQ ID NO. 1
VAQGQWEPSGXAP

SEQ ID NO. 2
PSGPAPTNXGALE

SEQ ID NO. 3
TLEQQHXVAQGQW

SEQ ID NO. 4
EVDPGSAELQKVLQGD

SEQ ID NO. 5
ELSSKADEASELAC
```

In the above sequences, "X" represents any amino acid. In a preferred embodiment, the FAS peptide is encoded by a nucleic acid containing any combination of nucleotide degeneracy.

The invention also provides a mixture of two or more FAS peptides, each containing an amino acid sequence that is identical with or homologous to a sequence represented in SEQ ID NOs. 1-5.

The peptides may be derivatized e.g., by conjugation with bovine serum albumin (BSA), or keyhole limpet hemocyanin (KLH), and/or with a functional group such as hydroxy (—OH), acetyl (—CH2COOH) or amide (—NH2).

Antibodies Against FAS

The present invention also provides antibodies that are specifically immunoreactive with the FAS peptides and FAS proteins containing at the FAS peptide sequences as described above. The antibodies may be polyclonal or monoclonal or recombinant, produced by methods known in the art or as described below.

As use herein, the term "specifically immunoreactive" refers to a measurable and reproducible specific immunoreaction such as binding between a peptide and an antibody that is determinative of the presence of the peptide in the presence of a heterogeneous population of peptides and other biologics. The term "specifically immunoreactive" may include specific recognition of structural shapes and surface features. Thus, under designated conditions, an antibody specifically immunoreactive to a particular peptide does not bind in a significant amount to other peptides present in the sample. An antibody specifically immunoreactive to a peptide has an association constant of at least about $10^3$ $M^{-1}$ or $10^4$ $M^{-1}$, sometimes about $10^5$ $M^{-1}$ or $10^6$ $M^{-1}$, in other instances $10^6$ $M^{-1}$ or $10^7$ $M^{-1}$, preferably about $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to determine antibodies specifically immunoreactive to a particular peptide. For example, solid-phase ELISA immunoassays are routinely used to select monoclonal antibodies specifically immunoreactive with a peptide. See, e.g., Harlow and Lane (1988), Antibodies, A Laboratory Manual, Cold Spring Harbor Publications, New York, for a description of immunoassay formats and conditions that can be used to determine specific immunoreactivity.

As used herein, the term "antibody" refers to an immunoglobulin specifically immunoreactive to a given antigen (e.g., a FAS peptide of the invention). The term "antibody" as used herein is intended to include whole antibodies of any isotype (IgG, IgA, IgM, IgE, etc), and fragments thereof. An "antibody" of the invention also includes an antibody preparation, e.g., a serum (antiserum). Antibodies can be fragmented using conventional techniques and the fragments screened for utility in the same manner as whole antibodies. Thus, the term includes segments of proteolytically-cleaved or recombinantly-prepared portions of an antibody molecule that selectively reacts with a certain protein or peptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. Antibodies may be labeled with detectable labels by one of skill in the art. The label can be a radioisotope, fluorescent compound, chemiluminescent compound, enzyme, or enzyme co-factor, or any other labels known in the art. In some aspects, the antibody that binds to an entity one wishes to measure (the primary antibody) is not labeled, but is instead detected by binding of a labeled secondary antibody that specifically binds to the primary antibody.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. The antibodies of the invention can be from any animal origin including birds and mammals. Preferably, the antibodies are of human, murine (e.g., mouse and rat), donkey, sheep, rabbit, goat, guinea pig, camel, horse, or chicken origin.

As used herein, a "monoclonal antibody" refers to an antibody that recognizes only one type of antigen. This type of antibodies is produced by the daughter cells of a single antibody-producing hybridoma. A monoclonal antibody typically displays a single binding affinity for any epitope with which it immunoreacts. A monoclonal antibody may contain an antibody molecule having a plurality of antibody combining sites, each immunospecific for a different epitope, e.g., a bispecific monoclonal antibody. Monoclonal antibodies may be obtained by methods known to those skilled in the art. Kohler and Milstein (1975), *Nature*, 256:495-497; U.S. Pat. No. 4,376,110; Ausubel et al. (1987, 1992), eds., Current Protocols in Molecular Biology, Greene Publishing Assoc. and Wiley Interscience, N.Y.; Harlow and Lane (1988), Antibodies: A Laboratory Manual, Cold Spring Harbor Laboratory; Colligan et al. (1992, 1993), eds., Current Protocols in Immunology, Greene Publishing Assoc. and Wiley Interscience, N.Y.; Iyer et al., *Ind. J. Med. Res.*, (2000), 123:561-564.

The antibodies of the present invention can be monospecific or multispecific (e.g., bispecific, trispecific, or of greater multispecificity). Multispecific antibodies can be specific for different epitopes of a peptide of the present invention, or can be specific for both a peptide of the present invention, and a heterologous epitope, such as a heterologous peptide or solid support material. See, e.g., WO 93/17715; WO 92/08802; WO 91/00360; WO 92/05793; Tutt et al., 1991, *J. Immunol.*, 147:60-69; U.S. Pat. Nos. 4,474,893; 4,714,681; 4,925,648; 5,573,920; 5,601,819; and Kostelny et al., 1992, *J. Immunol.*, 148:1547-1553. For example, the antibodies may be produced against a peptide containing repeated units of a FAS peptide sequence of the invention, or they may be produced against a peptide containing two or more FAS peptide sequences of the invention, or the combination thereof.

Moreover, antibodies can also be prepared from any region of the FAS peptides of the invention. In addition, if a polypeptide is a receptor protein, antibodies can be developed against an entire receptor or portions of the receptor, for example, an intracellular domain, an extracellular domain, the entire transmembrane domain, specific transmembrane segments, any of the intracellular or extracellular loops, or any portions of these regions. Antibodies can also be developed against specific functional sites, such as the site of ligand binding, or sites that are glycosylated, phosphorylated, myristylated, or amidated, for example.

In the present invention, the FAS peptides for generating antibodies preferably contain a sequence of at least about 6, at least about 7, more preferably at least about 8, at least about 9, at least about 10, at least about 11, at least about 12, at least about 13, and preferably, between about 5 to about 50 amino acids in length, more preferably between about 8 to about 15 amino acids in length. The preferred FAS peptides are those having an amino acid sequence the same as or homologous to all or a portion of the sequence of the peptides of SEQ ID NOs. 1-5.

The human, humanized or non-human monoclonal antibodies of the present invention can be prepared using well-established methods. In one embodiment, the monoclonal antibodies are prepared using hybridoma technology, such as those described by Kohler and Milstein (1975), *Nature*, 256:495. In a hybridoma method, a mouse, hamster, or other appropriate host animal, is typically immunized with an immunizing agent (e.g., a FAS peptide of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell. Goding, Monoclonal Antibodies: Principles and Practice, Academic Press, (1986) pp. 59-1031. Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.* (1984), 133:3001; Brodeur et al., Monoclonal Antibody Production Techniques and Applications, Marcel Dekker, Inc., New York, (1987) pp. 51-63; Fukuma et al., *Autoimmunity*, 10(4):291-195 (1991).

The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding specificity of the monoclonal antibody can, for example, be determined by the Scatchard analysis of Munson and Pollard (1980), *Anal. Biochem.*, 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Polyclonal antibodies of the invention can also be produced by various procedures well known in the art. For the production of polyclonal antibodies in vivo, host animals, such as rabbits, rats, mice, sheep, or goats, are immunized with either free or carrier-coupled peptides, for example, by intraperitoneal and/or intradermal injection. Injection material is typically an emulsion containing about 100 μg of peptide or carrier protein. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of antibody which can be detected, for example, by ELISA assay using free peptide adsorbed to a solid surface. The titer of antibodies in serum from an immunized animal can be increased by selection of antibodies, e.g., by adsorption of the peptide onto a solid support and elution of the selected antibodies according to methods well known in the art.

Antibodies encompassed by the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds to the antigen of interest can be selected or identified with antigen, e.g., using labeled antigen or antigen bound or captured onto a solid surface or bead. Phage used in these methods are typically filamentous phage including fd and M13 binding domains expressed from phage with Fab, Fv, or disulfide stabilized antibody domains recombinantly fused to either the phage polynucleotide III or polynucleotide VIII protein. Examples of phage display methods that can be used to make the antibodies of the present invention include those disclosed in Brinkman et al. (1995) *J. Immunol. Methods*, 182:41-50; Ames et al. (1995) *J. Immunol. Methods*, 184:177-186; Kettleborough et al. (1994) *Eur. J. Immunol.*, 24:952-958; Persic et al. (1997) *Gene*, 187:9-18; Burton et al. (1994) *Advances in Immunology*, 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below.

Examples of techniques that can be used to produce antibody fragments such as single-chain Fvs and antibodies include those described in U.S. Pat. Nos. 4,946,778 and 5,258, 498; Huston et al. (1991) *Methods in Enzymology*, 203:46-88; Shu et al. (1993) *Proc. Natl. Acad. Sci. USA*, 90:7995-7999; and Skerra et al. (1988) Science, 240:1038-1040, each of which is incorporated herein by reference in its entirety.

For some uses, including the in vivo use of antibodies in humans and in vitro detection assays, it is preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. See, e.g., Morrison (1985), *Science*, 229:1202; Oi et al. (1986), BioTechniques, 4:214; Gillies et al. (1989), *J. Immunol. Methods*, 125:191-202; and U.S. Pat. Nos. 5,807,715; 4,816,567; and 4,816,397, which are incorporated herein by reference in their entirety.

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. See, e.g., Queen et al., U.S. Pat. Nos. 5,693,762 and 5,585,089; and Riechmann et al. (1988) *Nature*, 332:323, which are incorporated herein by reference in their entireties. Antibodies can be humanized using a variety of techniques known in the art, including, for example, CDR-grafting (EP 239, 400; PCT publication WO 91/09967; U.S. Pat. Nos. 5,225,539; 5,530,101; and 5,585, 089); veneering or resurfacing (EP 592,106; EP 519,596; Padlan (1991), *Molecular Immunology*, 28(4/5):489-498; Studnicka et al. (1994) *Protein Engineering*, 7(6):805-814; Roguska et al. (1994) *Proc. Natl. Acad. Sci. USA*, 91:969-973; and chain shuffling (U.S. Pat. No. 5,565,332). Humanized monoclonal antibodies of the present invention preferably are prepared by the technique described by Carter et al., (1992) *Proc. Natl. Acad. Sci. USA*, 89:4285-4289, which is incorporated herein by reference in its entirety, including the references cited therein.

Completely human antibodies are particularly desirable for therapeutic treatment of human patients, so as to avoid or alleviate immune reaction to foreign protein. Human antibodies can be made by a variety of methods known in the art, including the phage display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Thus, using such a technique, it is possible to produce useful human IgG, IgA, IgM, IgD and IgE antibodies. For an overview of the technology for producing human antibodies, see Lonberg and Huszar (1995) *Intl. Rev. Immunol.,* 13:65-93. For a detailed discussion of the technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, which are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies. Preferred methods for producing human monoclonal antibodies of the present invention are those described in Nash et al., *Immunology,* 68:332-340 (1989) and Fukuma et al., *Autoimmunity,* 10(4):291-195 (1991), which are incorporated herein by reference in their entirety.

Once an antibody molecule of the invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

In one embodiment, the present invention provides human or humanized monoclonal antibodies that specifically immuoreact to a FAS protein, or fragment or variant thereof. In a preferred embodiment, the invention provides a novel monoclonal antibody that specifically recognizes a sequence comprising at least about 6 up to the entire sequence of a peptide selected from the group consisting of SEQ ID NOs. 1-5.

The invention further provides a mixture containing two or more monoclonal antibodies produced as described above. In a preferred embodiment, the mixture contains two or more monoclonal antibodies raised against different FAS peptides derived from the same FAS protein. In another preferred embodiment, the mixture contains two or more monoclonal antibodies raised against different FAS peptides, at least two of which are derived from different FAS proteins.

In a currently preferred embodiment, the antibody mixture contains two or more antibodies raised against peptides comprising an amino acid sequence selected from the group consisting of: SEQ ID NOs. 1-5.

Utility

In a preferred embodiment, the antibodies of the present invention are human, humanized or chimeric monoclonal antibodies appropriate for administration to humans. These antibodies can be used alone or as a component in a mixture with other antibodies or other pharmaceutical agents to treat cancers or image cancerous tissues.

Regardless of whether the present antibodies are used for therapy or diagnosis, they can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the biological agent, such as an antibody or binding portion thereof, of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The antibodies of the present invention may also be administered in injectable dosages by solution or suspension of these materials in a physiologically acceptable diluent with a pharmaceutical carrier. Such carriers include sterile liquids such as water and oils, with or without the addition of a surf actant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the antibodies of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically from about 0.1 mg/kg to about 100 mg/kg of the patient's body weight. Preferably, the dosage administered to a patient is between about 0.1 mg/kg and about 20 mg/kg of the patient's body weight, more preferably about 1 mg/kg to about 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

In a preferred aspect, the patient to be treated with a monoclonal antibody of the invention is first tested for FAS positivity, e.g., the level of expression of FAS by the patient's disease is determined. Techniques known to those of skill in the art can be used for measuring FAS activity in a patient sample. For example, FAS expression can be assayed, for example, by immunoassays including, but not limited to, competitive and non-competitive assay systems using techniques such as western blots, immunohistochemistry (IHC), radioimmunoassays, ELISA (enzyme linked immunosorbent assay), "sandwich" immunoassays, immunoprecipitation assays, precipitin reactions, gel diffusion precipitation reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs). In a preferred embodiment, the level of expression of FAS is measured by IHC techniques using either an antibody of the present invention or a commercial anti-FAS antibody, such as those available from Cell Signaling Technologies (Danvers, Mass.).

The present antibodies also may be utilized to detect cancerous tissues in vivo or in an in vitro diagnostic test. This may be achieved, for example, by labeling the antibody or binding fragment thereof, administering the labeled agent to a mammal, and then imaging the mammal. Alternatively, anti-FAS antibodies of the present invention may be used a "capture" antibodies in an immunoassay, and the amount of FAS captures in the assay may be detected using either an antibody of the present invention or a commercial anti-FAS antibody, such as those available from Cell Signaling Technologies (Danvers, Mass.).

Examples of labels useful for diagnostic or prognostic applications in accordance with the present invention are radiolabels such as $^{131}$I, $^{111}$In, $^{123}$I, $^{99}$mTc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes, such as a transrectal probe, can also be employed. These isotopes and transrectal detector probes, when used in combination, are especially useful in detecting prostatic fossa recurrences and pelvic nodal disease. The antibody can be labeled with such reagents using techniques known in the art. For example, see Wensel and Meares, Radioimmunoimaging and Radioimmunotherapy, Elsevier, New York (1983), which is hereby incorporated by reference, for techniques relating to the radiolabeling of antibodies. See also, D. Colcher et al., "Use of Monoclonal Antibodies as Radiopharmaceuticals for the Localization of Human Carcinoma Xenografts in Athymic Mice", Meth. Enzymol., 121: 802 816 (1986), which is hereby incorporated by reference.

A radiolabeled antibody or fragment of this invention can be used for in vitro diagnostic tests. The specific activity of a tagged biological agent, such as a tagged antibody, binding portion thereof, probe, or ligand, depends upon the half-life, the isotopic purity of the radioactive label, and how the label is incorporated into the biological agent. Commonly-used isotopes include isotopes of carbon, silicon, hydrogen, phosphorus or iodine. In immunoassay tests, the higher the specific activity, in general, the better the sensitivity.

Procedures for labeling antibodies and other biological agents with radioactive isotopes are generally known in the art. Tritium labeling procedures are described in U.S. Pat. No. 4,302,438, which is hereby incorporated by reference. Iodinating, tritium labeling, and 35S labeling procedures especially adapted for murine monoclonal antibodies are described by Goding, J. W. (supra, pp 124-126) and the references cited therein, which are hereby incorporated by reference. Other procedures for iodinating biological agents, such as antibodies, binding portions thereof, probes, or ligands, are described by Hunter and Greenwood, Nature, 144:945 (1962), David et al., Biochemistry, 13:1014 1021 (1974), and U.S. Pat. Nos. 3,867,517 and 4,376,110, which are hereby incorporated by reference. Radiolabeling elements which are useful in imaging include $^{125}$I, $^{131}$I, $^{111}$In, and $^{99}$mTc, for example. Procedures for iodinating biological agents are described by Greenwood, F. et al., Biochem. J., 89:114 123 (1963); Marchalonis, J., Biochem. J., 113:299 305 (1969); and Morrison, M. et al., Immunochemistry, 289 297 (1971), which are hereby incorporated by reference. Procedures for $^{99}$mTc-labeling are described by Rhodes, B. et al. in Burchiel, S. et al. (eds.), Tumor Imaging: The Radioimmunochemical Detection of Cancer, New York: Masson 111 123 (1982) and the references cited therein, which are hereby incorporated by reference. Procedures suitable for 111In-labeling biological agents are described by Hnatowich, D. J. et al., J. Immul. Methods, 65:147 157 (1983), Hnatowich, D. et al., J. Applied Radiation, 35:554 557 (1984), and Buckley, R. G. et al., F.E.B.S., 166:202 204 (1984), which are hereby incorporated by reference.

In the case of a radiolabeled antibody, the antibody or fragment thereof is administered to the patient, is localized to the tumor bearing the antigen with which the biological agent reacts, and is detected or "imaged" in vivo using known techniques such as radionuclear scanning using e.g., a gamma camera or emission tomography. See e.g., A. R. Bradwell et al., "Developments in Antibody Imaging", Monoclonal Antibodies for Cancer Detection and Therapy, R. W. Baldwin et al., (eds.), pp. 65-85 (Academic Press 1985), which is hereby incorporated by reference. Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

Fluorophore and chromophore labeled antibodies or fragments thereof can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science,* 162:526 (1968) and Brand, L. et al., *Annual Review of Biochemistry,* 41:843 868 (1972), which are hereby incorporated by reference. The biological agents can be labeled with fluorescent chromophore groups by conventional procedures such as those disclosed in U.S. Pat. Nos. 3,940,475, 4,289,747, and 4,376,110, which are hereby incorporated by reference.

One group of fluorescers having a number of the desirable properties described above are the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies or fragments thereof can be labeled with fluorchromes or chromophores by the procedures described by Goding, J. (supra, pp 208-249). The antibody or fragment can be labeled with an indicating group containing the NMR-active $^{19}F$ atom, or a plurality of such atoms inasmuch as (i) substantially all of naturally abundant fluorine atoms are the 19F isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body NMR determination is carried out using an apparatus such as one of those described by Pykett, *Scientific American,* 246:78-88 (1982), which is hereby incorporated by reference, to locate and image cancerous tissues.

The antibody or fragment can also be utilized to kill or ablate cancerous cells in vivo. This involves using the present antibodies or fragments thereof by themselves or with a cytotoxic drug to which the antibody or fragment of the present invention are bound. This involves administering the present antibodies or fragments thereof bonded to a cytotoxic drug to a mammal requiring such treatment.

The antibody or fragment of the present invention may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), Morodica charantia inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO84/03508 and WO85/03508, which are hereby incorporated by reference. Certain cytotoxic moieties are derived from adriamycin, chlorambucil, daunomycin, methotrexate, neocarzinostatin, and platinum, for example.

Procedures for conjugating the present antibodies or fragments thereof with the cytotoxic agents have been previously described. Procedures for conjugating chlorambucil with antibodies are described by Flechner, I., *European Journal of Cancer,* 9:741-745 (1973); Ghose, T. et al., *British Medical Journal,* 3:495 499 (1972); and Szekerke, M., et al., *Neoplasma,* 19:211-215 (1972), which are hereby incorporated by reference. Procedures for conjugating daunomycin and adriamycin to antibodies are described by Hurwitz, E. et al., *Cancer Research,* 35:1175-1181 (1975) and Amon, R. et al. *Cancer Surveys,* 20 1:429-449 (1982), which are hereby incorporated by reference. Procedures for preparing antibody-ricin conjugates are described in U.S. Pat. No. 4,414,148 and by Osawa, T., et al. *Cancer Surveys,* 1:373-388 (1982) and the references cited therein, which are hereby incorporated by reference. Coupling procedures as also described in EP 86309516.2, which is hereby incorporated by reference.

Alternatively, the present antibodies or fragments thereof can be coupled to high energy radiation emitters, for example, a radioisotope, such as $^{131}I$, a .gamma.-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy*, R. W. Baldwin et al. (eds.), pp 303 316 (Academic Press 1985), which is hereby incorporated by reference. Other suitable radioisotopes include α-emitters, such as $^{212}Bi$, $^{213}Bi$, and $^{211}At$, and β-emitters, such as $^{186}Re$ and $^{90}Y$. Radiotherapy is expected to be particularly effective, because prostate epithelial cells and vascular endothelial cells within cancers are relatively radiosensitive.

Where the present antibodies or fragments thereof are used alone to kill or ablate cancerous cells or prostate epithelial cells, such killing or ablation can be effected by initiating endogenous host immune functions, such as complement-mediated or antibody-dependent cellular cytotoxicity.

The antibodies or fragments thereof of the present invention can be used and sold together with equipment, as a kit, to detect the particular label.

The antibodies or fragments thereof of the present invention can be used in conjunction with other therapeutic treatment modalities. Such other treatments include surgery, radiation, cryosurgery, thermotherapy, hormone treatment, chemotherapy, vaccines, and other immunotherapies.

Also encompassed by the present invention is a method of killing or ablating which involves using the antibody or fragment for prophylaxis. For example, these materials can be used to prevent or delay development or progression of cancers.

The Examples below sets forth the results of a preclinical evaluation of a monoclonal antibody produced according to the present invention. The results obtained indicate that the monoclonal antibody is effective as an anti-tumor agent. The monoclonal antibody of the present invention was able to mediate different biological responses in vitro, including inhibition of FAS-dependent cell growth, as well as reduce tumor growth via apoptosis in mice implanted with human gastrointestinal stromal tumor (GIST) cells, while exhibiting no adverse effects in murine toxicology models.

EXAMPLES

Example 1

Four murine monoclonal antibodies were prepared by immunizing SCID mice with synthetic FAS peptides, and establishing hybridomas according to the general procedure described by Iyer et al., *Ind. J. Med. Res.*, 123:651-564 (2006). Each mouse was immunized with one peptide as follows:

| Mouse/Hybridoma | Peptide | | |
|---|---|---|---|
| A | SEQ ID NO. 1 | VAQGQWEPSGXAP |
| B | SEQ ID NO. 2 | PSGPAPTNXGALE |
| D | SEQ ID NO. 4 | EVDPGSAELQKVLQGD |
| E | SEQ ID NO. 5 | ELSSKADEASELAC |

Humanized monoclonal antibodies were prepared as described by Carter et al., *Proc. Natl. Acad. Sci. USA*, 89:4285-89 (1992) from monoclonal antibodies A,B, D and E. The humanized monoclonal antibodies (MAbs) are referred to hereinafter as FAS 1, FAS 2, FAS 4 and FAS 5.

| Mouse/Hybridoma | Humanized MAb |
|---|---|
| A | FAS 1 |
| B | FAS 2 |
| D | FAS 4 |
| E | FAS 5 |

FAS 4 humanized monoclonal antibody has been deposited with the American Type Culture Collection, ATCC Accession No. PTA-10810.

Example 2

The humanized FAS monoclonal antibodies prepared as described in Example 1 were screened against human sera using an ELISA assay according to the following protocol.

Microwell strips (12 8-well strips, Cell Signalling Technology, Inc.) were brought to room temperature. Wash buffer was prepared by diluting 20x wash buffer (Cell Lysis Buffer, CST #9803, Cell Signalling Technology, Inc.) with purified water to make 1x buffer.

Monoclonal antibodies FAS 1, FAS 2, FAS 4 and FAS 5 (Example 1) were used as capture antibodies. The capture antibodies were immobilized in the microwells as described below.

Preparation of Solutions

Capture Antibody Coating Solution: Antibodies to be used as capture antibodies are combined with 50 mM sodium carbonate (pH 9.6), 20 mM Tris HCl (pH 8.5) or 10 mM PBS (pH 7.2), to a protein concentration of between 1-10 µg/ml.

Blocking Solution: Blocking agent (BSA, FBS, nonfat dry milk, casein, or gelatin) is diluted with buffer to a concentration of approximatelyl % for BSA, and approximately 5% (or greater) of FBS, nonfat dry milk, casein, or gelatin. Sodium azide is added to a concentration of approximately 0.05%.

Primary/Secondary Detection Antibody Solution: Primary (and secondary, if appropriate) detection antibodies are diluted in 1x blocking solution (to minimize nonspecific binding) to a concentration of 0.1-1.0 µg/ml.

Wash solution: 0.1M PBS or Tris-buffered saline (pH 7.4) is combined with Tween 20 (0.02%-0.05% v/v).

Coating of Microwell Plates with Capture Antibody

Add 100 µl of capture antibody coating solution to each well of a microwell plate or strip, and incubate for 1 hour at room temperature. Empty plate and tap out residual liquid. Block plate by adding 300 µA of blocking solution to the wells, incubating for 5 minutes, and tapping out residual liquid. The plates are ready to be used.

Preparing Cell Lysates

To prepare the sample, the pooled serum was centrifuged to separate cells, which then were lysed using sonication. The media was removed, and cold PBS was added. The PBS was removed and 0.5 mL of cold 1x Cell Lysis buffer plus 1 mM phenylmethylsulfonyl fluoride (PMSF) was added to each plate (10 cm in diameter) and incubated on ice for 5 minutes. The cells were carefully scraped off the plate, and transferred to an appropriate tube, kept on ice. The tubes of cell lysates were sonicated on ice, then microcentrifuged for 10 minutes at 4° C., after which the supernatant containing the cell lysate was transferred to a new tube. The supernatant is the cell lysate. The cell lysate was stored at −80° C. in single-use aliquots until needed.

Test Procedure

Bring microwell plates coated with capture antibody to room temperature. Add 100 µl of sample diluent (Cell Signalling Technology, Inc.) to a microcentrifuge tube., transfer 100 µl of cell lysate into the tube and vortex for a few seconds. 100 µl of each diluted cell lysate were added to the appropriate well, and sealed with tape. The plates were incubated for 2 hours at 37° C. (Alternatively, the plate may be incubated overnight at 4° C.).

The tape was removed and the plate contents decanted into a receptacle. The plates then were washed 4 times with 1x wash solution, 200 µl each time for each well. For each wash, the residual solution in each well was removed, but the wells were not allowed to become completely dry at any time. 100 µl of a solution containing the detection antibody (Cell Signaling Technology, Inc.) to each well. The plates were sealed with tape and incubated for 1 hour at 37° C.

The wash procedure described above then was repeated. 100 µl of HRP-Linked secondary antibody (red color) to each well. The plates were sealed with tape and incubated for 30 minutes at 37° C.

The wash procedure described above was again repeated. 100 µl of TMB

Substrate (Cell Signaling Technology, Inc.) was added to each well. The plates were sealed with tape and incubated for 10 minutes at 37° C. or 30 minutes at 25° C. 100 µl of STOP Solution (Cell Signalling Technology, Inc.) was added to each well, and the plates were shaken gently for a few seconds. The initial color of positive reaction is blue, which changes to yellow upon addition of STOP Solution.

For visual determination, the plates must be read within 30 minutes after adding STOP Solution. For spectrophotometric determination, the absorbance must be read at 450 nm within 30 minutes after adding STOP Solution. For this Example, the absorbance was read using a fluorescence plate reader (Thermo Fisher Scientific, Inc.).

ELISA assays were performed to determine FAS expression in cells derived from the pooled sera of two prostate cancer patients. To prepare the sample, the pooled serum was centrifuged to separate cells, which then were lysed using sonication as described above.

The assay parameters were as follows:

Assay Parameters:

| Step | Reagent | Serial dilution | Dilution buffer | Concentration | Volume/vile | Incubation |
|---|---|---|---|---|---|---|
| Ag coating | FAS 1, 2, 4 or 5 | — | 0.15M PBS | 2 .µg/mL | 50 µL | 1 hr @ 37 C. |
| Blocking | SeaBlock* | — | — | NEAT | 300 µL | 30 min. @ 37 C. |
| Sample Dilution | see below | 5X | 0.15M PBS | starting @ 1:50 | 80 µ · L | 30 min. @ R.T. |
| Secondary Ab | anti-Rb HRP** | — | 15M PBS w 0.05% Tween20 | 1:10000 | 50 µ · L | 30 min. @ R.T. |

*Supplied by East Coat Biologies, North Berwick, ME
**Supplied by Cell Signaling Technology, Inc.

Absorbance was measured at 450 nm using a Thermo Shandon plate reader.

The data obtained for the ELISA using FAS 1, 2, 5 and 5 are shown in the tables below. In the tables, the term "pre-purification" refers to the murine monoclonal antibody prior to humanization and affinity purification, and "post-purification" refers to the monoclonal antibody after humanization and affinity purification. Data for pre-purified and post-purified antibodies are included for comparison.

The data for FAS 1 and 2 are shown in Table 1:

TABLE 1

ELISA Results for FAS 1 and 2
Plate Design:

| | Sample Dilution | | | | | | | | | | | |
|---|---|---|---|---|---|---|---|---|---|---|---|---|
| | 1:50 | | 1:250 | | 1:1250 | | 1:6250 | | 1:31250 | | 1:156000 | |
| | 1 | 2 | 3 | 4 | 5 | 6 | 7 | 8 | 9 | 10 | 11 | 12 |
| Pre-purification FAS 1 | 0.03 | 0.02 | 0.014 | 0.01 | 0.01 | 0.01 | 0.008 | 0.005 | 0.01 | 0 | 0.01 | 0 |
| Pre-purification FAS 2 | 0.07 | 0.06 | 0.022 | 0.04 | 0.01 | 0.02 | 0.01 | 0.007 | 0 | 0 | 0.01 | 0.01 |
| Post-purification FAS 1 | 0.67 | 0.02 | 0.766 | 0.02 | 0.96 | 0.01 | 0.598 | 0.18 | 0.176 | 0.01 | 0.05 | 0 |
| Post-purification FAS 2 | 0.59 | 0.02 | 0.659 | 0.03 | 0.78 | 0.02 | 0.439 | 0.12 | 0.12 | 0 | 0.03 | 0.02 |

FIG. 1 shows the data in Table 1 in graphical form. For each dilution, the two left columns represent the pre-purification MAbs, and the two right columns represent the post-purification MAbs. The graph shows that the FAS 1 and 2 antibodies were able to detect significant levels of FAS in the patient sera even at very high dilutions.

The data obtained for the ELISA using FAS 4 are shown in Table 1:

TABLE 2

ELISA Results for FAS 4
Plate Design:

| | Sample Dilution | | | | | | | | | | | |
|---|---|---|---|---|---|---|---|---|---|---|---|---|
| | 1:50 | | 1:250 | | 1:1250 | | 1:6250 | | 1:31250 | | 1:156000 | |
| | 1 | 2 | 3 | 4 | 5 | 6 | 7 | 8 | 9 | 10 | 11 | 12 |
| Pre-purification FAS 4 | 0.03 | 0.02 | 0.014 | 0.01 | 0.01 | 0.01 | 0.008 | 0.005 | 0.01 | 0 | 0.01 | 0 |
| Pre-purification FAS 4a | 0.07 | 0.06 | 0.022 | 0.04 | 0.01 | 0.02 | 0.01 | 0.007 | 0 | 0 | 0.01 | 0.01 |
| Post-purification FAS 4 | 0.67 | 0.02 | 0.766 | 0.02 | 0.96 | 0.01 | 0.598 | 0.007 | 0.18 | 0.01 | 0.05 | 0 |
| Post-purification FAS 4a | 0.59 | 0.02 | 0.659 | 0.03 | 0.78 | 0.02 | 0.439 | 0.009 | 0.12 | 0 | 0.03 | 0.02 |

Figure 2:
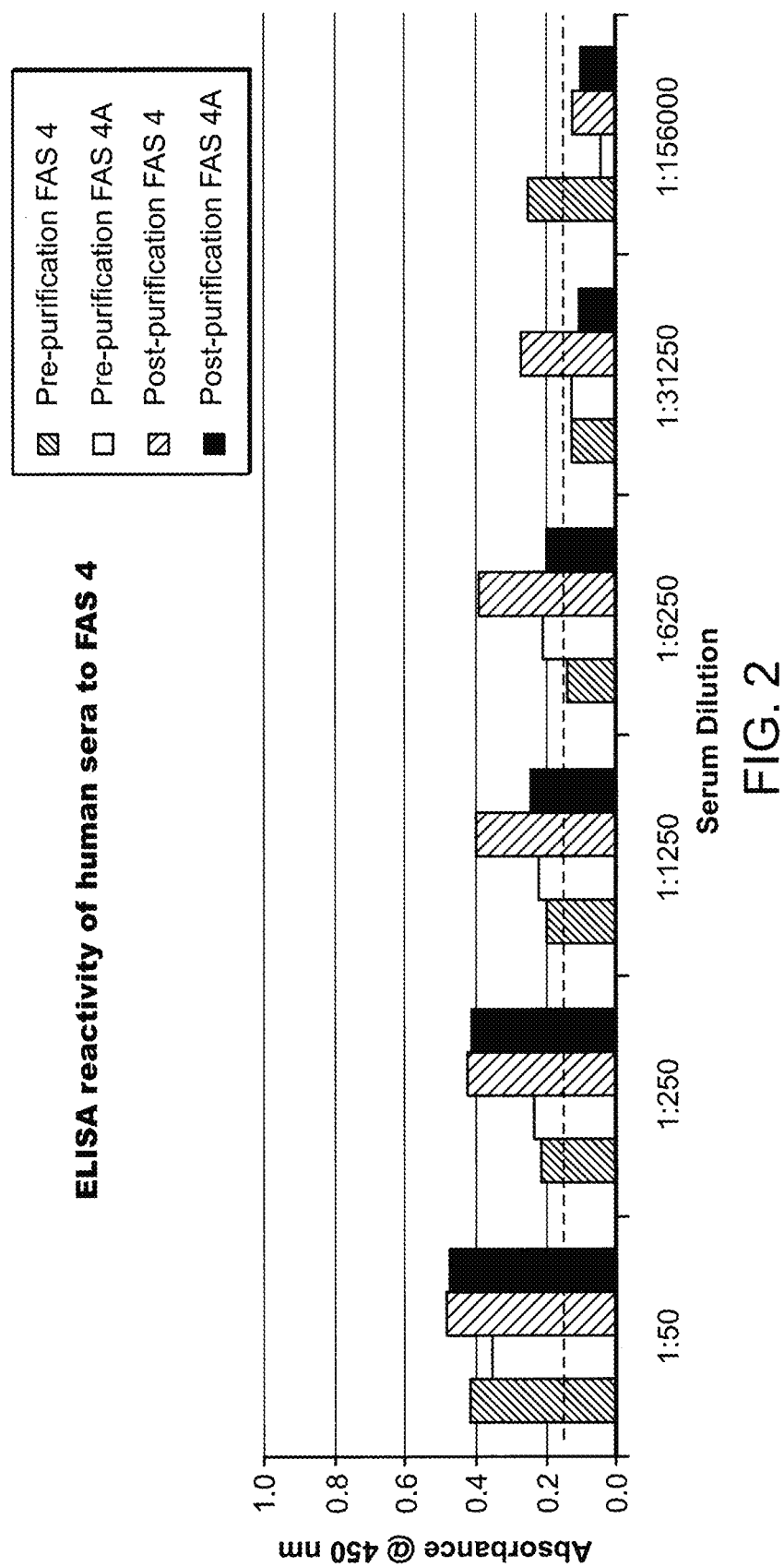
FIG. 2 is a graph showing the results of an ELISA assay using a monoclonal antibody of the present invention raised against the peptide of SEQ. ID NO. 4 as the capture antibody. For each dilution, the two left columns represent the pre-purification MAbs, and the two right columns represent the post-purification MAbs.

FAS 4 and FAS 4a represent two separate batches of FAS 4. FIG. 2 shows the data in graphical form. For each dilution, the two left columns represent the pre-purification MAbs, and the two right columns represent the post-purification MAbs. The graph shows that the FAS 4 antibody was able to detect significant levels of FAS in the patient sera even at very high dilutions.

The data obtained for the ELISA using FAS 5 are shown in Table 3:

TABLE 3

ELISA Results for FAS 5
Plate Design:

| | Sample Dilution | | | | | | | | | | | |
|---|---|---|---|---|---|---|---|---|---|---|---|---|
| | 1:50 | | 1:250 | | 1:1250 | | 1:6250 | | 1:31250 | | 1:156000 | |
| | 1 | 2 | 3 | 4 | 5 | 6 | 7 | 8 | 9 | 10 | 11 | 12 |
| Pre-purification FAS 5 | 0.02 | 0 | 0.02 | 0.01 | 0.03 | 0.02 | 0.01 | 0.013 | 0.02 | 0.01 | 0.02 | 0.02 |
| Pre-purification FAS 5a | 0 | 0.02 | 0.03 | 0.02 | 0.05 | 0.02 | 0.02 | 0 | 0.01 | 0.01 | 0.03 | 0.09 |
| Post-purification FAS 5 | 0.59 | 0.06 | 1.434 | 0.08 | 1.15 | 0.04 | 1.484 | −0.15 | 1.07 | 0.03 | 0.27 | 0.01 |
| Post-purification FAS 5a | 0.46 | 0.3 | 0.441 | 0.01 | 0.41 | 0 | 0.234 | 0.018 | 0.09 | 0.02 | 0.09 | 0.08 |

Figure 3:
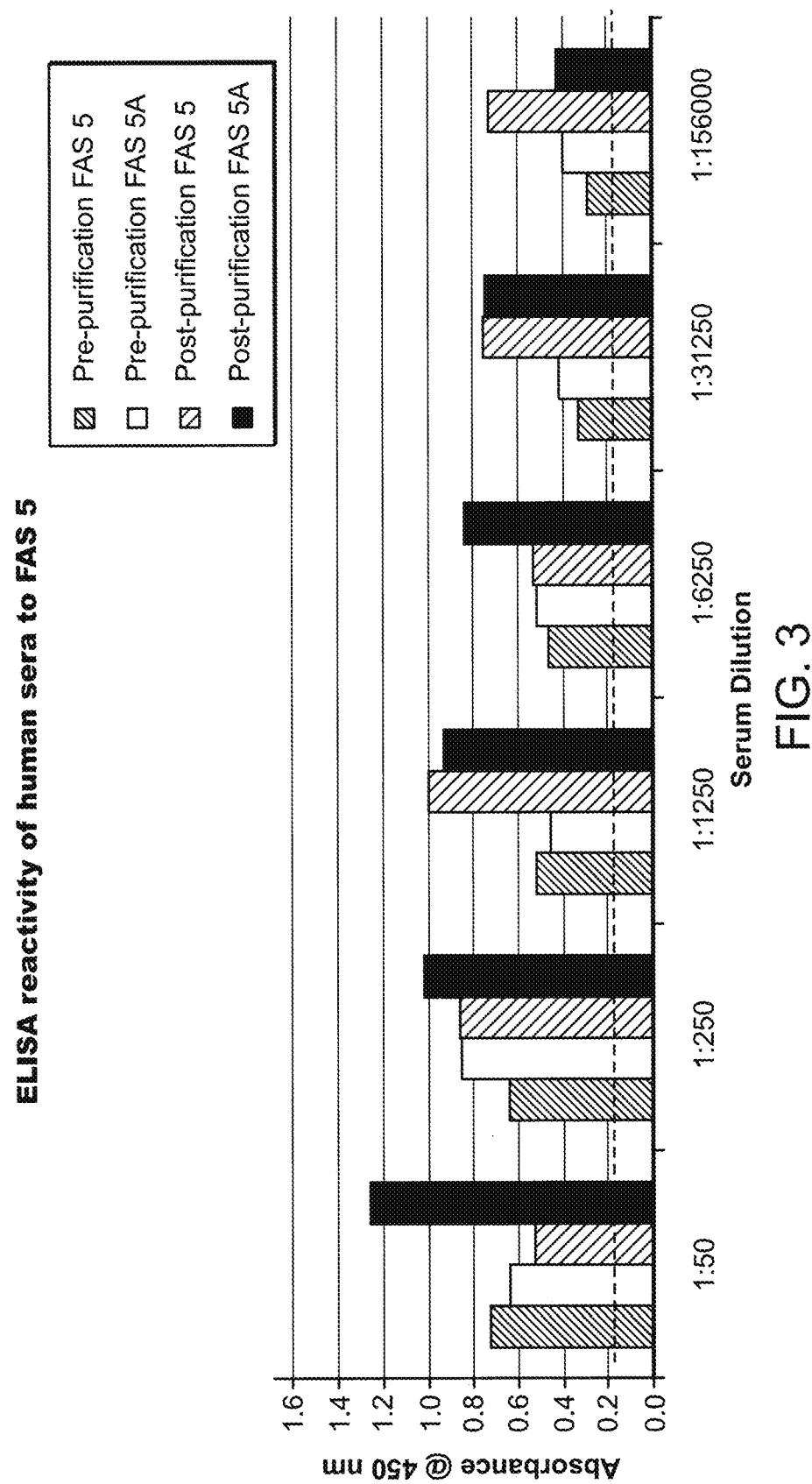
FIG. 3 is a graph showing the results of an ELISA assay using a monoclonal antibody of the present invention raised against the peptide of SEQ. ID NO. 5 as the capture antibody. For each dilution, the two left columns represent the pre-purification MAbs, and the two right columns represent the post-purification MAbs.
Figure 4:
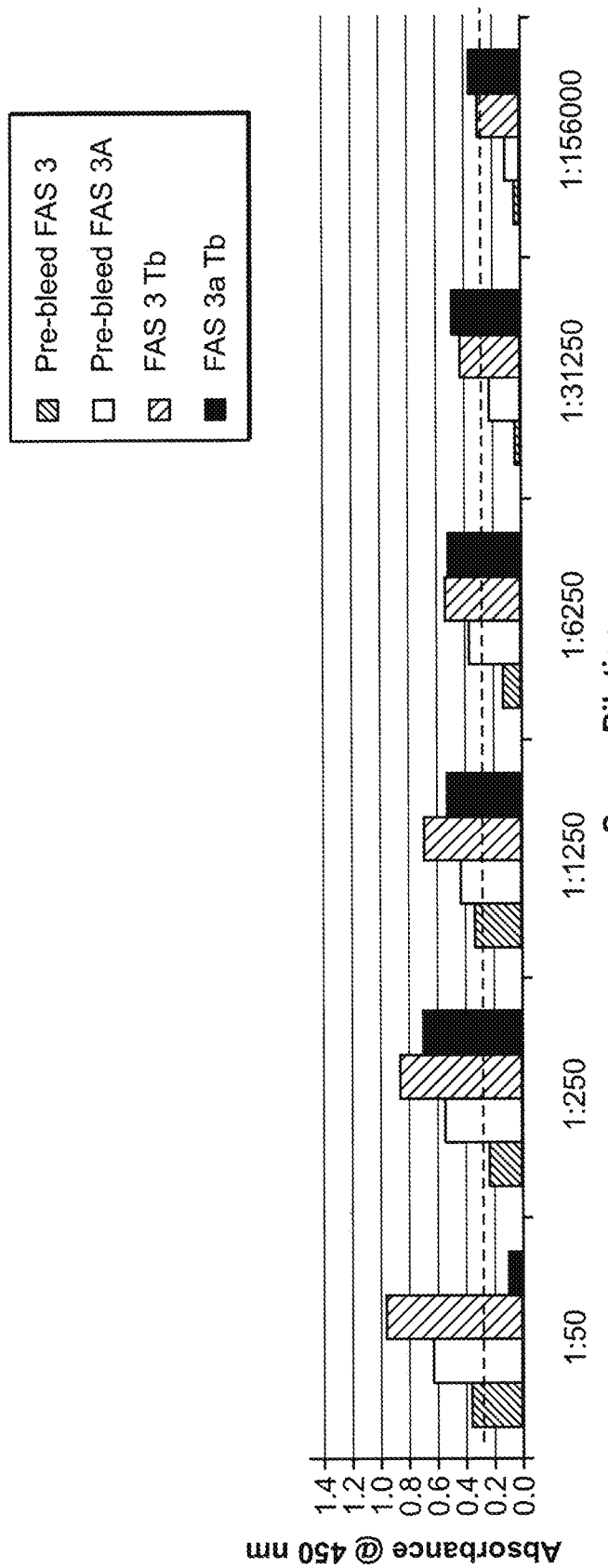
FIG. 4 is a graph showing the results of an ELISA assay using polyclonal antisera of the present invention raised against the peptide of SEQ. ID NO. 3 as the capture antibody. For each dilution, the two left columns represent the pre-purification MAbs, and the two right columns represent the post-purification MAbs.

FAS 5 and FAS 5a represent two separate batches of FAS 5. FIG. 3 shows the data in graphical form. For each dilution, the two left columns represent the pre-purification MAbs, and the two right columns represent the post-purification MAbs. The graph shows that the FAS 5 antibody was able to detect significant levels of FAS in the patient sera even at very high dilutions.

Example 3

The peptide of SEQ ID NO. 3 was used to prepare polyclonal antisera according to the following procedure: SPF rabbits (Maine Biotechnology Services, Inc.) were used to generate polyclonal antisera. Each rabbit was injected the following peptide (SEQ ID NO. 3). The rabbits were bled, and the antisera were then affinity purified using the same epitope (SEQ ID NO. 3) against which they had been raised.

ELISA assays were performed to determine FAS expression in cells derived from the pooled sera of two prostate cancer patients described in Example 2 using the FAS 3 polyclonal antisera. The assay parameters are shown below:

Assay Parameters:

| Step | Reagent | Serial dilution | Dilution buffer | Concentration | Volume/vile | Incubation |
|---|---|---|---|---|---|---|
| Ag coating | FAS 3 | — | 0.15M PBS | 2 µg/mL | 50 µL | 1 hr @ 37 C. |
| Blocking | SeaBlock* | — | — | NEAT | 300 µL | 30 min. @ 37 C. |
| Sample Dilution | see below | 5X | 0.15M PBS | starting @ 1:50 | 80 µ · L | 30 min. @ R.T. |
| Secondary Ab | anti-Rb HRP** | — | 15M PBS w 0.05% Tween20 | 1:10000 | 50 µ · L | 30 min. @ R.T. |

*Supplied by East Coat Biologies, North Berwick, ME
**Supplied by Cell Signaling Technology, Inc.

The data obtained for the ELISA using the FAS 3 antisera are shown in Table 4. In Table 4, the term "pre-bleed" refers to the FAS 3 antisera before incubation, and the term "Tb" (total bleed) refers to the polyclonal antisera after incubation.

TABLE 4

ELISA Results for FAS 3 Polyclonal Antisera
Plate Design:

| Sample Dilution | | | | | | | | | | | |
|---|---|---|---|---|---|---|---|---|---|---|---|
| 1:50 | | 1:250 | | 1:1250 | | 1:6250 | | 1:31250 | | 1:156000 | |
| 1 | 2 | 3 | 4 | 5 | 6 | 7 | 8 | 9 | 10 | 11 | 12 |

| | 1 | 2 | 3 | 4 | 5 | 6 | 7 | 8 | 9 | 10 | 11 | 12 |
|---|---|---|---|---|---|---|---|---|---|---|---|---|
| Pre-bleed FAS 3 | 0.03 | 0.34 | 0.016 | 0.02 | 0.01 | 0.02 | 0.01 | 0.014 | 0.01 | 0.01 | 0.01 | 0.01 |

REFERENCES

1. Albertsen P C, Hanley J A, Fine J. 20-year outcomes following conservative management of clinically localized prostate cancer. *JAMA*, (2005 May 4), 293(17):2095-101.

2. Andersson S O, Wolk A, Bergstrom R, Adami H O, Engholm G, Englund A, et al. Body size and prostate cancer: a 20-year follow-up study among 135006 Swedish construction workers. *J Natl Cancer Inst.*, (1997 Mar. 5), 89(5):385-9.

3. Calle E E, Rodriguez C, Walker-Thurmond K, Thun M J. Overweight, obesity, and mortality from cancer in a prospectively studied cohort of U.S. adults. N Engl J. Med., (2003 Apr. 24), 348(17):1625-38.

4. Cerhan J R, Cantor K P, Williamson K, Lynch C F, Tomer J C, Burmeister L F. Cancer mortality among Iowa farmers: recent results, time trends, and lifestyle factors (United States). *Cancer Causes Control*, (1998 May), 9(3):311-9.

5. Snowdon D A, Phillips R L, Choi W. Diet, obesity, and risk of fatal prostate cancer. *Am J Epidemiol.*, (1984 August), 120(2):244-50.

6. Wright M E, Chang S C, Schatzkin A, Albanes D, Kipnis V, Mouw T, et al. Prospective study of adiposity and weight change in relation to prostate cancer incidence and mortality. Cancer, (2007 Jan. 8)

7. Chirala S S, Huang W Y, Jayakumar A, Sakai K, Wakil S J. Animal fatty acid synthase: functional mapping and cloning and expression of the domain I constituent activities. *Proc Natl Acad Sci USA*, (1997 May 27), 94(11):5588-93.

8. Kuhajda F P, Pizer E S, Li J N, Mani N S, Frehywot G L, Townsend C A. Synthesis and antitumor activity of an inhibitor of fatty acid synthase. *Proc Natl Acad Sci USA*, (2000 Mar. 28), 97(7):3450-4.

9. Rossi S, Graner E, Febbo P, Weinstein L, Bhattacharya N, Onody T, et al. Fatty acid synthase expression defines distinct molecular signatures in prostate cancer. *Mol Cancer Res*. (2003 August), 1(10):707-15.

10. Kridel S J, Axelrod F, Rozenkrantz N, Smith J W. Orlistat is a novel inhibitor of fatty acid synthase with antitumor activity. *Cancer Res.*, (2004 Mar. 15), 64(6):2070-5.

11. De Schrijver E, Brusselmans K, Heyns W, Verhoeven G, Swinnen J V. RNA interference-mediated silencing of the fatty acid synthase gene attenuates growth and induces morphological changes and apoptosis of LNCaP prostate cancer cells. *Cancer Res.*, (2003 Jul. 1), 63(13):3799-804.

12. Shah U S, Dhir R, Gollin S M, Chandran U R, Lewis D, Acquafondata M, et al. Fatty acid synthase gene over expression and copy number gain in prostate adenocarcinoma. *Hum Pathol.*, (2006 April), 37(4):401-9.

13. Baron A, Migita T, Tang D, Loda M. Fatty acid synthase: a metabolic oncogene in prostate cancer? *J Cell Biochem*. (2004 Jan. 1), 91(1):47-53.

14. Sabine J R, Abraham S, Chaikoff I L. Control of lipid metabolism in hepatomas: insensitivity of rate of fatty acid and cholesterol synthesis by mouse hepatoma BW7756 to fasting and to feedback control. *Cancer Res.*, (1967 April), 27(4):793-9.

15. Ookhtens M, Kannan R, Lyon I, Baker N. Liver and adipose tissue contributions to newly formed fatty acids in an ascites tumor. *Am J Physiol.*, (1984 July), 247(1 Pt 2):R146-53.

16. Weiss L, Hoffmann G E, Schreiber R, Andres H, Fuchs E, Korber E, et al. Fatty-acid biosynthesis in man, a pathway of minor importance. Purification, optimal assay conditions, and organ distribution of fatty-acid synthase. *Biol Chem Hoppe Seyler*. (1986 September), 367(9):905-12.

17. Kuhajda F P. Fatty-acid synthase and human cancer: new perspectives on its role in tumor biology. *Nutrition*. (2000 March), 16(3):202-8.

18. Swinnen J V, Van Veldhoven P P, Timmermans L, De Schrijver E, Brusselmans K, Vanderhoydonc F, et al. Fatty acid synthase drives the synthesis of phospholipids partitioning into detergent-resistant membrane microdomains. *Biochem Biophys Res Commun.*, (2003 March) 21; 302(4):898-903.

19. Kuhajda F P, Jenner K, Wood F D, Hennigar R A, Jacobs L B, Dick J D, et al. Fatty acid synthesis: a potential selective target for antineoplastic therapy. *Proc Natl Acad Sci USA.*, (1994 Jul. 5), 91(14):6379-83.

20. Smotrys J E, Linder M E. Palmitoylation of intracellular signaling proteins: regulation and function. *Annual Rev Biochem.*, (2004), 73:559-87.

21. Swinnen N, Vanderhoydonc F, Elgamal A A, Eelen M, Vercaeren I, Joniau S, et al. Selective activation of the fatty acid synthesis pathway in human prostate cancer. *Int J Cancer*, (2000 Oct. 15), 88(2):176-9.

22. Swinnen J V, Esquenet M, Goossens K, Heyns W, Verhoeven G. Androgens stimulate fatty acid synthase in the human prostate cancer cell line LNCaP. *Cancer Res.*, (1997), 57(6):1086-90.

23. Heemers H, Maes B, Foufelle F, Heyns W, Verhoeven G, Swinnen J V. Androgens stimulate lipogenic gene expression in prostate cancer cells by activation of the sterol regulatory element-binding protein cleavage activating protein/sterol regulatory element-binding protein pathway. *Mol Endocrinol*. (2001), 15(10):1817-28.

24. Yang Y A, Han W F, Morin P J, Chrest F J, Pizer E S. Activation of fatty acid synthesis during neoplastic transformation: role of mitogen-activated protein kinase and phosphatidylinositol 3-kinase. *Exp Cell Res.*, (2002 Sep. 10), 279(1):80-90.

25. Graner E, Tang D, Rossi S, Baron A, Migita T, Weinstein L J, et al. The isopeptidase USP2a regulates the stability of fatty acid synthase in prostate cancer. *Cancer Cell.*, (2004 March), 5(3):253-61.

26. Priolo C, Tang D, Brahamandan M, Benassi B, Sicinska E, Ogino S, et al. The Isopeptidase USP2a Protects Human Prostate Cancer from Apoptosis. *Cancer Res.*, (2006 Sep. 1), 66(17):8625-32.

27. Luo Z, Saha A K, Xiang X, Ruderman N B. AMPK, the metabolic syndrome and cancer. *Trends Pharmacol Sci.*, (2005 February), 26(2):69-76.

28. Kahn B B, Alquier T, Carling D, Hardie D G. AMP-activated protein kinase: ancient energy gauge provides clues to modern understanding of metabolism. *Cell Metab.*, (2005 January), 1(1):15-25.

29. Momcilovic M, Hong S P, Carlson M. Mammalian TAK1 activates Snf1 protein kinase in yeast and phosphorylates AMP-activated protein kinase in vitro. *J Biol Chem.*, (2006 Sep. 1), 281(35):25336-43.

30. Xie M, Zhang D, Dyck J R, Li Y, Zhang H, Morishima M, et al. A pivotal role for endogenous TGF-beta-activated kinase-1 in the LKB1/AMP-activated protein kinase energy-sensor pathway. *Proc Natl Acad Sci USA*, (2006 Nov. 14), 103(46):17378-83.

31. Braga-Basaria M, Dobs A S, Muller D C, Carducci M A, John M, Egan J, et al. Metabolic syndrome in men with prostate cancer undergoing long-term androgen-deprivation therapy. *J Clin Oncol.*, (2006 Aug. 20), 24(24):3979-83.

32. Moore P. Connecting LKB1 and AMPK links metabolism with cancer. *J Biol.* (2003), 2(4):24.1-.4.

33. Boudeau J, Sapkota G, Alessi D R. LKB1, a protein kinase regulating cell proliferation and polarity. *FEBS Lett.*, (2003 Jul. 3), 546(1):159-65.

34. Xiang X, Saha A K, Wen R, Ruderman N B, Luo Z. AMP-activated protein kinase activators can inhibit the growth of prostate cancer cells by multiple mechanisms. *Biochem Biophys Res Commun.* (2004 Aug. 13), 321(1):161-7.

35. Diraison F, Parton L, Ferre P, Foufelle F, Briscoe C P, Leclerc I, et al. Over-expression of sterol-regulatory-element-binding protein-1c (SREBP1c) in rat pancreatic islets induces lipogenesis and decreases glucose-stimulated insulin release: modulation by 5-aminoimidazole-4-carboxamide ribonucleoside (AICAR). *Biochem J.* (2004 Mar. 15), 378(Pt 3):769-78.

36. Jimenez A I, Fernandez P, Dominguez O, Dopazo A, Sanchez-Cespedes M. Growth and molecular profile of lung cancer cells expressing ectopic LKB1: down-regulation of the phosphatidylinositol 3'-phosphate kinase/PTEN pathway. *Cancer Res.*, (2003 Mar. 15), 63(6):1382-8.

37. Scherer P E, Williams S, Fogliano M, Baldini G, Lodish H F. A novel serum protein similar to C1q, produced exclusively in adipocytes. *J Biol Chem.*, (1995 Nov. 10), 270(45):26746-9.

38. Yamauchi T, Kamon J, Minokoshi Y, Ito Y, Waki H, Uchida S, et al. Adiponectin stimulates glucose utilization and fatty-acid oxidation by activating AMP-activated protein kinase. *Nat Med.*, (2002 November), 8(11):1288-95.

39. Gu H F, Abulaiti A, Ostenson C G, Humphreys K, Wahlestedt C, Brookes A J, et al. Single nucleotide polymorphisms in the proximal promoter region of the adiponectin (APM1) gene are associated with type 2 diabetes in Swedish caucasians. *Diabetes*, (2004 February), 53 Suppl 1:S31-5.

40. Kang E S, Park S Y, Kim H J, Ahn C W, Nam M, Cha B S, et al. The influence of adiponectin gene polymorphism on the rosiglitazone response in patients with type 2 diabetes. *Diabetes Care*, (2005 May), 28(5):1139-44.

41. Ford E S, Giles W H, Dietz W H. Prevalence of the metabolic syndrome among US adults: findings from the third National Health and Nutrition Examination Survey. *JAMA*, (2002 Jan. 16), 287(3):356-9.

---

The invention claimed is:

1. An isolated monoclonal antibody that specifically binds to the amino acid sequence of SEQ ID NO. 5.

2. The monoclonal antibody of claim 1 which is humanized.

3. A monoclonal antibody obtained by a method comprising the steps of:
   a. contacting a mammal with the peptide consisting of SEQ ID NO. 5;
   b. collecting cells containing the antibody from the mammal; and
   c. immortalizing the cells obtained in step (b) thereby creating a hybridoma expressing the monoclonal antibodies that specifically bind to the amino acid sequence of SEQ ID NO. 5.

4. The monoclonal antibody of claim 3 wherein the mammal is immuno-compromised and the monoclonal antibody produced is a humanized antibody.

5. A method for detecting the presence or amount of a FAS protein or polypeptide in a biological sample comprising contacting the sample with the monoclonal antibody of claim 1 and determining the amount of the FAS protein bound to the monoclonal antibody.

6. The method of claim 5 wherein the monoclonal antibody is labeled with a detectable label.

7. A method for detecting the presence or amount of a FAS protein or polypeptide in a biological sample comprising contacting the sample with the monoclonal antibody of claim 2 and determining the amount of the FAS protein bound to the monoclonal antibody.

8. The method of claim 7 wherein the monoclonal antibody is labeled with a detectable label.

9. A method for detecting the presence or amount of a FAS protein or polypeptide in a biological sample comprising contacting the sample with the monoclonal antibody of claim 3 and determining the amount of the FAS protein bound to the monoclonal antibody.

10. The method of claim 9 wherein the monoclonal antibody is labeled with a detectable label.

* * * * *